(12) United States Patent
Prejean et al.

(10) Patent No.: US 7,442,690 B2
(45) Date of Patent: Oct. 28, 2008

(54) TOPICAL TREATMENT FOR PSORIASIS

(75) Inventors: Helen Prejean, Horseshoe Bend, AR (US); Mark Malcolm, Roland, AR (US)

(73) Assignee: P & L Enterprise LLC, Melbourne, AR (US)

( * ) Notice: Subject to any disclaimer, the term of this patent is extended or adjusted under 35 U.S.C. 154(b) by 595 days.

(21) Appl. No.: 11/079,361

(22) Filed: Mar. 14, 2005

(65) Prior Publication Data

US 2006/0205699 A1  Sep. 14, 2006

(51) Int. Cl.
*A01N 25/00* (2006.01)
*A01N 37/36* (2006.01)
*A61K 31/60* (2006.01)

(52) U.S. Cl. ........................ 514/159; 424/405
(58) Field of Classification Search ........................ None
See application file for complete search history.

(56) References Cited

U.S. PATENT DOCUMENTS

| | | | |
|---|---|---|---|
| 4,102,995 A | 7/1978 | Hebborn | |
| 4,983,382 A | 1/1991 | Wilmott et al. | |
| 5,122,536 A | 6/1992 | Perricone | |
| 6,011,067 A * | 1/2000 | Hersh | 514/562 |
| 6,221,377 B1 | 4/2001 | Meyer | |
| 6,337,337 B1 | 1/2002 | Buck | |
| 2003/0191098 A1 | 10/2003 | D'Amato | |
| 2004/0081681 A1 | 4/2004 | Vromen | |
| 2004/0180935 A1 | 9/2004 | Venkatraman et al. | |

OTHER PUBLICATIONS

Funk, Amy, Volatile organic compounds, Center for Disease Control, http://0-www.cdc.gov.pugwash.lib.warwick.ac.uk/nceh/clusters/Fallon, 2003, pp. 1-11.*
National Psoriasis Foundation, Topical Treatments: Tar, updated Jun. 2006, http://www.psoriasis.org/treatment/psoriasis/topicals/tar.php.

* cited by examiner

*Primary Examiner*—MP Woodward
*Assistant Examiner*—Kyle Purdy
(74) *Attorney, Agent, or Firm*—Mark Murphey Henry; Nathan Price Chaney

(57) ABSTRACT

The present treatment cocktail represents a dual mode topical treatment for the skin disease psoriasis. The composition contains at least an Analgesic Agent and a Drying Agent as selected from the group disclosed herein. The agents heal psoriatic plaques by promoting the exfoliation of existing psoriatic plaques and preventing additional plaque formation. Further, the dual mode action is useful to reduce the pain and itching associated with such plaques which results in less irritation and shorter outbreaks.

1 Claim, No Drawings

TOPICAL TREATMENT FOR PSORIASIS

CROSS REFERENCES

None.

GOVERNMENT RIGHTS

None.

BACKGROUND OF THE INVENTION

The present invention relates to the treatment of the skin disease psoriasis. Psoriasis is a chronic condition that is typically characterized by scaling and inflammation of the skin. Upwards of seven million people in the United States suffer from this disease and more than 11% of that group are rendered disabled. The symptoms of psoriasis include patches of red, inflamed skin covered with loose, whitish scales which can crack and bleed; psoriasis can also affect nails and cause arthritis. Classical symptoms cycle through periods of activity and remission, and the implications of active psoriasis can range from minor itching to life-threatening immune system overload. The visibility of the outbreaks and the ability of the disease to become resistant to previously effective treatments can cause psychological repercussions as well.

Many treatment options exist for psoriasis including topical treatments, to which the present invention is directed. This is generally a first step in treating psoriasis; however, for outbreaks that cover a significant portion of the body, topical applications of medication may not prove enough. Phototherapy is another mode of treating psoriasis outbreaks, and it involves exposing psoriatic plaques to UV or laser light. Finally, Qral or injected medicines such as steroids may be used in severe cases or when the outbreaks do not respond to other treatments.

The background of the art reveals a significant deficiency in topical treatments with various agents because the modes of delivery have proven unreliable. Moreover, the prior art topical applications generally target only one symptom such as inflammation, i.e., topical application of steroids. The present invention represents a significant advancement over prior methods of topical treatments because it is directed at a dual mode approach whereby the treatment comprises one or more Analgesic Agents that are intended to reduce pain, itching, and inflammation and one or more Drying Agents that are intended to exfoliate the skin and modulate the rampant cell growth associated with psoriasis. Together, these agents help to promote healing much more effectively than use of steroids.

BRIEF SUMMARY OF THE INVENTION

The present invention contemplates a dual mode topical treatment for psoriasis. The dual mode approach is designed to not simply treat the acute symptoms associated with psoriatic plaques but are designed to enhance the body's production of new, healthier skin as derived from the deeper skin levels of the epidermis. It is believed by the inventors that certain autoimmune disorders potentially associated with or leading to psoriasis can be minimized or eliminated if the deepest skin layers respond well to treatment.

The human integumentary system comprises three layers of skin known generally as the epidermis, the dermis, and the hypodermis. Psoriasis afflicts a varying number of the five epidermal skin layers, but begins with the deepest of the epidermal layers. Beginning with the deepest sublayer of the epidermis, the five strata are as follows: the stratum basale, the stratum spinosum, the stratum granulosum, the stratum lucidum, and the stratum corneum, which concerns the outermost layer of skin cells. These different skin layers routinely renew through a natural process known as desquamation wherein the deepest level skin cells are pushed toward the skin surface. While undergoing desquamation, normal and healthy squamous cells located in the stratum basale divide and begin to produce the keratin that will eventually dominate their contents as the cells are pushed towards the stratum corneum.

Psoriasis is the result of a phenomenon whereby the deepest cells proliferate too rapidly. Healthy skin, and the normal structured layers of the epidermis, cannot shed these hyperplastic proliferating cells quickly enough so the hyperplastic cells accumulate and form in thick, dry patches known as plaques. Furthermore, the epidermal skin layers become highly inflamed due to the overpopulation of cells and the infusion of other immune response cells. The normal epithelium is severely disrupted with the overproduction of these hyperplastic cells.

The present invention contemplates essentially two types of modes of action, i.e., an Analgesic Agent and a Drying Agent. The Analgesic Agent may include one or more of the following group selection: salicylic acid and ibuprofen. These two agents share a common mode of action insofar as they inhibit the cyclo-oxygenase enzyme, which is a chemical that leads to pain and inflammation. The Drying Agent may be selected from one or more of the following group: ethyl alcohol, isopropyl alcohol, ethyl benzene, m-xylene, o-xylene, and p-xylene. These six agents share a common mode of action insofar as their chemical structure serves to dehydrate the tissue, which alleviates immediate inflammation through displacement of water. This process is thought to be important in facilitating rapid exfoliation and also in reducing inflammation. Furthermore, the Drying Agent also permits the Analgesic Agents to reach the deepest sublayers of the epidermal skin layer, which in turn also alleviates pain, inflammation, and promotes healing.

The present invention contemplates a method of delivery as well as a composition of matter.

It is an object of the present invention to provide a topical mode of delivery of Analgesic Agents and Drying Agents in a manner that best facilitates absorption by the epidermis such that the stratum basale receives effective treatment.

It is further object of the present invention to provide a skin treatment cocktail that embodies at least one Analgesic Agent (s) and at least one Drying Agent(s).

It is further object of the present invention to provide a skin treatment cocktail that helps modulate and decrease the rapid proliferation of certain skin layers by effectively treating the stratum basale and the remaining epidermal skin layers with anti-inflammatory agents and cyclo-oxygenase inhibitors.

It is further object of the present invention to provide a treatment for the skin condition psoriasis wherein the patient exhibits a satisfactory response after failing to achieve a response using other methods of treatment.

With the foregoing objects of the present objects of the invention in mind, the following is the best mode as established to date.

DETAILED DESCRIPTION OF THE INVENTION

Because psoriasis and other skin disorders manifests as itchy, flaky skin plaques known to innervate all different epithelium strata, the present invention contemplates a need to treat all layers of the epithelium strata.

The inventors believe that the most effective treatment for skin diseases involve direct topical application to the most superficial epidermal layer of at least two different agents known as an Analgesic Agent and a Drying Agent. The Analgesic Agent is selected to reduce inflammation, pain, and irritation surrounding the superficial skin plaques, which can lead to further irritation and subsequent outbreaks. These Analgesic Agents were also selected based on their ability to inhibit the cyclo-oxygenase enzyme, which is important in order to minimize pain and inflammation. The Analgesic Agent is selected from the group salicylic acid and ibuprofen, which share the additional common characteristics of anti-inflammation, rapid effect, and relatively short half-life. These agents also have an established record on bioavailability and low toxicity.

So too, a Drying Agent is necessary to help modulate the rampant growth of the stratum basale and to minimize water encapsulated within the stratum spinosum and the stratum granulosum, which in turn fosters a detachment of the psoriatic plaques from, for example, the stratum lucidum and the stratum corneum, i.e., the upper skin strata. Psoriatic plaques innervate not simply the stratum corneum and the stratum ludicum but have been shown to incorporate deeper skin layers as the origination of psoriasis is known to begin with the stratum basale. The Drying Agent also serves a second purpose, which is to assist in the delivery of the Analgesic Agent to the deepest layers of the skin epidermis.

One or more Drying Agents is/are selectively chosen from the group ethyl alcohol, isopropyl alcohol, ethyl benzene, and m-xylene, o-xylene, and p-xylene. The present invention incorporates one or more of these listed agents to dehydrate and exfoliate psoriatic plaques, which the inventors understand induces the growth of normal, healthy skin. The Drying Agents share common characteristics originating with chemical structure and polarity and have similar effects upon lipid-based membranes that form the cellular structure of the skin.

The therapeutic method of delivery comprises applying to the afflicted psoriatic skin plaque and immediate surrounding skin region an effective amount of a treatment cocktail, such treatment cocktail comprising an effective amount of the Analgesic Agent(s) selected from the group salicylic acid and ibuprofen and an effective amount of the Drying Agent(s) selected from the group ethyl alcohol, isopropyl alcohol, ethyl benzene, m-xylene, o-xylene, and p-xylene.

A preferred therapeutic method of delivery is to then administer both the treatment cocktail comprising the Analgesic Agent and the Drying Agent via a Carrier generally taking the form of lotion, cream, foam, or liquid. The use of a Carrier will also confer the benefit of allowing patients to reliably apply the proper amount of the cocktail to the surface of the affected skin. The Carrier may also provide the added benefit of moisturizing the affected skin. The Carrier is not restricted in this situation as it may also include a precursor or derivative of the stated or claimed Analgesic and/or Drying Agent of this invention, depending on the stability of the Analgesic Agent and/or Drying Agent both alone and in compound with other ingredients. The preferred Carrier is Velvachol®, which is an over-the-counter, water-miscible compounding vehicle in a non-sticky, non-greasy, odorless topical base that is compatible with a wide range of chemicals.

In the first preferred embodiment, the Analgesic Agents are selected from the group salicylic acid and ibuprofen as present in a form between the ranges 0.5 and 10 g/100 mL for ibuprofen, and between the ranges 0.5 and 10 g/100 mL for salicylic acid. The Drying Agents are selected from the group ethyl alcohol, isopropyl alcohol, ethyl benzene, m-xylene, o-xylene, and p-xylene as present in a form between the ranges 19 and 60 g/100 mL ethyl alcohol; between the ranges of 2 and 10 g/100 mL isopropyl alcohol; between the ranges 0.0045 and 0.0090 g/100 mL ethyl benzene; between the ranges 0.0045 and 0.0090 g/100 mL o-xylene; between the ranges 0.0080 and 0.015 g/100 mL m-xylene; and between the ranges 0.0020 and 0.0080 g/100 mL p-xylene.

The second preferred embodiment of the present invention comprises an Analgeisc Agent and a Drying Agent selected from the groups disclosed in the first preferred embodiment. The second preferred embodiment may also contain zinc pyrithione, which may strengthen cellular membranes. The amount of ethyl alcohol in the second preferred embodiment of the composition may vary from 19 to 60 g/100 mL, and this serves as the predominant Drying Agent. It is also preferred that the other Drying Agents are included in the following amounts: isopropyl alcohol at 5.7 g/100 mL; ethyl benzene at approximately 0.0060 g/100 mL; o-xylene at approximately 0.0061 g/100 mL; m-xylene at approximately 0.012 g/100 mL; and p-xylene at approximately 0.0059 g/100 mL. It is preferred that the Analgesic Agents are included in the following amounts: salicylic acid at approximately 3 g/100 mL; and ibuprofen at 1.1 gm/100 mL. Additionally, a 2% zinc pyrithione solution may be included at approximately 0.42% by volume.

The second preferred embodiment is summarized in the following table:

| Ingredient | Amount |
| --- | --- |
| ethyl alcohol | 53 g/100 mL |
| isopropyl alcohol | 5.7 g/100 mL |
| ethyl benzene | ~0.0060 g/100 mL |
| o-xylene | ~0.0061 g/100 mL |
| m-xylene | ~0.012 g/100 mL |
| p-xylene | ~0.0059 g/100 mL |
| salicylic acid | 3 g/100 mL |
| Ibuprofen | 1.1 g/100 mL |
| 2% zinc pyrithrione solution | 0.42% by volume |
| Velvachol ® | sufficient to replace water |

Various treatment preparations were tested on individuals suffering from varying degrees of psoriasis vulgaris type plaques. With the above treatment cocktail, all patients achieved a successful result following a prescribed daily application to the affected psoriatic skin plaque area for a period ranging from ten (10) days to six (6) weeks, with the median time for patient recovery at approximately three weeks. No patients included within the studies reported any adverse side effects.

In a third preferred embodiment, all agents in the first and second preferred embodiments remain identical, and the Drying Agents other than ethyl alcohol remain at the amounts disclosed in the second preferred embodiment. Ethyl alcohol is established at 30 g/100 mL. The 2% zinc pyrithione solution is again included at 0.42% by volume. The composition is first dissolved in water, and using a second step, any water in the solution is replaced with Velvachol®, cream, lotion, or soap such that the composition is uniformly dissolved in a dermatologically-acceptable carrier for topical application.

The patient in this example presented with severe psoriatic plaques comprising an estimated 25% of whole body surface. The plaques were understood to be dry, painful, cracking, and invasive of several skin layers. The patient applied the composition of this example via a combination of each of three different carriers, namely, (1) liquid, (2) soap, (3) and cream. Resolution of substantially all psoriatic plaques occurred within fourteen (14) to twenty-one (21) days. The patient reported that the present invention provided substantially improved results than conventional treatments.

The fourth preferred embodiment is a variation of the second preferred embodiment in which the Drying Agents other than ethyl alcohol remain at the amounts disclosed in the second preferred embodiment. Again, ethyl alcohol is included at 30 g/100 mL and a 2% zinc pyrithione solution is included at 0.42% by volume. The Analgesic Agent consists solely of ibuprofen at 1.1 g/100 mL. The composition is first dissolved in water, and a second step is necessary to replace the water with Velvachol®, cream, lotion, or soap such that the composition is uniformly dissolved in a dermatologically-acceptable carrier for topical application.

The patient in this example presented with severe psoriatic symptoms occupying a majority of whole body surface. The psoriatic lesions were understood to be painful and to itch and bleed continually. Upon application of the present example for twenty-one (21) days, the patient reported that he was symptom-free for the first time in many years.

The foregoing preferred embodiments serve to illustrate how the claims could be put in practice; however, the claims are not intended to be restricted to the preferred embodiments.

We claim:

1. A skin treatment cocktail composition consisting of:
   (a) Between 19 and 60 g/100 mL ethyl alcohol;
   (b) Between 2 and 8 g/100 mL isopropyl alcohol;
   (c) Between 0.0045 and 0.0090 g/100 mL ethyl benzene;
   (d) Between 0.0045 and 0.0090 g/100 mL o-xylene;
   (e) Between 0.0080 and 0.015 g/100 mL m-xylene;
   (f) Between 0.0020 and 0.0080 g/100 mL p-xylene;
   (g) Between 0.5 and 10 gm/100 mL ibuprofen;
   (h) Between 0.5 and 10 gm/100 mL salicylic acid;
   (i) Between 0.2 and 0.8% by volume zinc pyrithione; and
   (j) A dermatologically-acceptable carrier or vehicle for facilitating topical application of the composition.

* * * * *